(12) United States Patent
Huffman et al.

(10) Patent No.: US 7,682,026 B2
(45) Date of Patent: Mar. 23, 2010

(54) EYE LOCATION AND GAZE DETECTION SYSTEM AND METHOD

(75) Inventors: Stephen Douglas Huffman, Fair Oaks Ranch, TX (US); Michael Patrick Rigney, San Antonio, TX (US)

(73) Assignee: Southwest Research Institute, San Antonio, TX (US)

(*) Notice: Subject to any disclaimer, the term of this patent is extended or adjusted under 35 U.S.C. 154(b) by 239 days.

(21) Appl. No.: 11/843,360

(22) Filed: Aug. 22, 2007

(65) Prior Publication Data

US 2008/0049185 A1 Feb. 28, 2008

Related U.S. Application Data

(60) Provisional application No. 60/839,167, filed on Aug. 22, 2006.

(51) Int. Cl.
*A61B 3/14* (2006.01)

(52) U.S. Cl. ........................ 351/210; 351/209

(58) Field of Classification Search ............... 351/209, 351/210, 206, 208, 221, 246, 200
See application file for complete search history.

(56) References Cited

U.S. PATENT DOCUMENTS

| 5,204,703 | A | 4/1993 | Hutchinson et al. | 351/210 |
|---|---|---|---|---|
| 5,912,721 | A | 6/1999 | Yamaguchi et al. | 351/210 |
| 6,296,358 | B1 | 10/2001 | Cornsweet et al. | 351/206 |
| 6,578,962 | B1 | 6/2003 | Amir et al. | 351/209 |
| 6,598,971 | B2 | 7/2003 | Cleveland | 351/209 |
| 6,604,825 | B2 | 8/2003 | Lai et al. | 351/210 |
| 6,758,563 | B2 | 7/2004 | Levola | 351/209 |
| 7,391,887 | B2* | 6/2008 | Durnell | 382/117 |
| 7,533,989 | B2* | 5/2009 | Ebisawa | 351/208 |
| 2004/0174496 | A1 | 9/2004 | Ji et al. | 351/209 |
| 2004/0196433 | A1 | 10/2004 | Durnell | 351/209 |

* cited by examiner

*Primary Examiner*—Hung X Dang
(74) *Attorney, Agent, or Firm*—Chowdhury & Georgakis PC

(57) ABSTRACT

A system and method for gaze detection of an animate subject, typically a human. The subject's pupils are located in three dimensional space, using red-eye detection techniques and triangulation. Then, the gaze direction is determined based on the shape of the subject's irises.

9 Claims, 4 Drawing Sheets

EYE LOCATION AND GAZE DETECTION SYSTEM AND METHOD

RELATED PATENT APPLICATION

This application claims the benefit of U.S. Provisional Application No. 60/839,167, filed Aug. 22, 2006 and entitled "EYE LOCATION AND GAZE DETECTION SYSTEM AND METHOD."

TECHNICAL FIELD OF THE INVENTION

This invention relates to systems and methods for automated detection of the location of the human eye and the gaze direction of the eye.

BACKGROUND OF THE INVENTION

Research in the field of automated detection of eye orientation and eye gaze direction (referred to herein as "automated gaze detection") has led to a variety of applications. Examples are laser eye surgery, weapon system targeting, and computer accessibility for the handicapped.

A common characteristic of conventional gaze detection systems is that a single camera is focused on a single eye. Many systems require a fixed or severely restricted distance between the camera and the eye. Because of this constraint, such systems are unsuitable for situations where head movement is likely, such as in virtual reality simulators. The fixed distance constraint is also limiting in desktop computing environments.

Previous efforts to accommodate head movement have resulted in solutions that use electronic or mechanical devices to dynamically measure the camera-to-eye distance. Some sort of head gear is typically required for these systems. For this reason, the usefulness of these systems is limited.

Most current gaze tracking research is based on a two-step approach, using a fixed camera viewing the face of the user to first find the eyes in a wide field-of-view image, and to then determine the direction of gaze using high resolution images of the eyes.

One method of quickly and accurately finding the eyes in an image is based on the "red-eye" phenomenon, well known to users of flash cameras. Two sets of infrared illuminators are used, with one set spaced apart from the other. Two images (obtained in rapid succession) are subtracted, leaving the "red-eye" reflections from the pupils as well as other noise and reflection points. With additional filtering and rule-based classification, the eyes can be located.

After the eyes are located in an image, the second step is to determine the direction of gaze. Various methods have been reported, including the use of contact lenses and artificial neural networks. Other methods are based on models of the eye and the shape of the iris and eyelid.

BRIEF DESCRIPTION OF THE DRAWINGS

A more complete understanding of the present embodiments and advantages thereof may be acquired by referring to the following description taken in conjunction with the accompanying drawings, in which like reference numbers indicate like features, and wherein.

DETAILED DESCRIPTION OF THE INVENTION

The invention described herein is directed to a system and method for "gaze detection", defined as the automated detection of eye position and gaze direction. Features of the system are that it is unobtrusive to the user, in the sense that no equipment need be worn by the user, and it does not interfere with normal user operations. The system requires minimal calibration to track the spatial position of both eyes at a very high rate. It can be used as an alternative to a pointer for computer control, and will improve the performance of virtual simulation systems.

Figure 1:
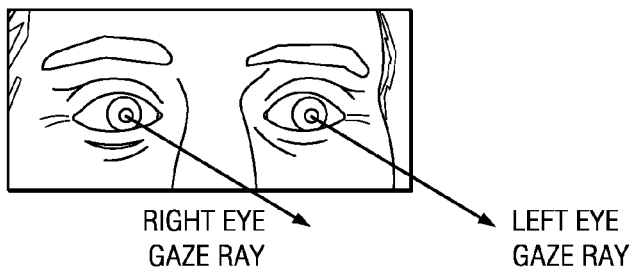
FIG. 1 illustrates the "gaze rays" associated with detection of eye position and look direction.

FIG. 1 illustrates the "gaze rays" associated with detection of eye position and look direction. Each eye has a location, which may be described in three-dimensional space. Each eye also has an associated gaze ray, with an origin at the pupil, and whose direction is to a point at which the subject is looking. A "gaze ray" may be distinguished from a "gaze vector", which is characterized by angle and length rather than origin and direction.

Figure 2:
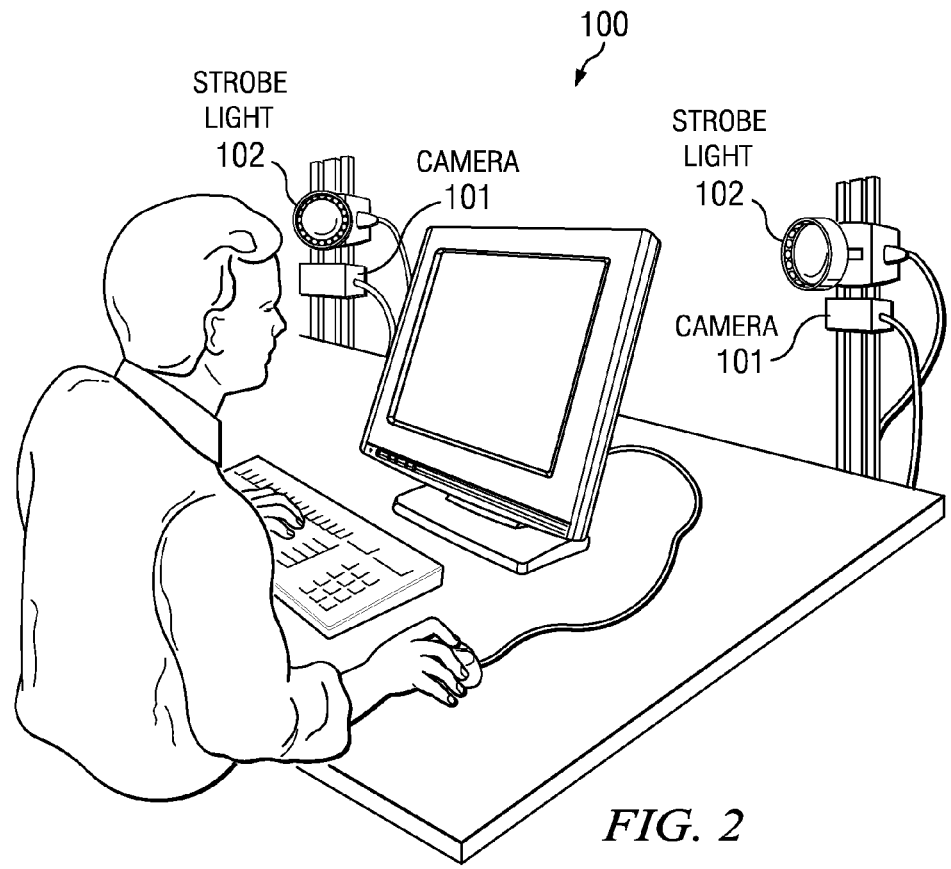
FIG. 2 illustrates a gaze detection system 100 in accordance with the invention.

FIG. 2 illustrates the gaze detection system 100. As explained below, system 100 first locates the subject's eyes in three-dimensional space by acquiring stereo image pairs of the subject's face and using lighting techniques to create a reflection from the retinas (the red-eye effect). System 100 then uses the same images to determine the gaze direction. In one embodiment, described herein, gaze direction is determined by modeling the iris as a circle on a sphere. Edge finding algorithms are used to curve-fit an ellipse to the iris, and projective geometry is used to determine each eye's orientation. However, the first step (eye location) may be used with other techniques for achieving the second step (gaze direction).

Figure 3:
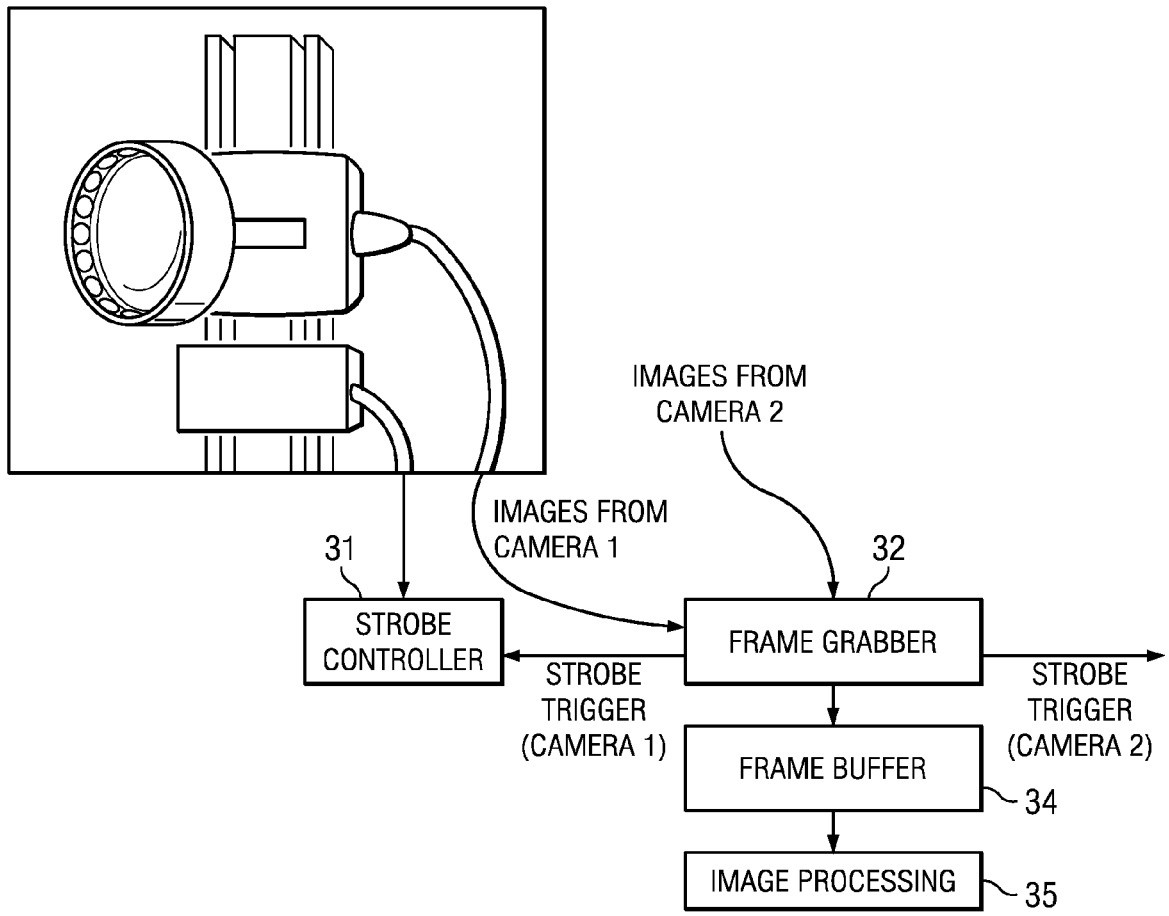
FIG. 3 illustrates one of the cameras of FIG. 2 and its associated strobe light in further detail.

More specifically, system 100 consists of two infra-red (IR) sensitive cameras 101, two IR strobe lights 102, a strobe sequencing circuit, a camera image capture card, and an image processing system (see FIG. 3). Each IR strobe light 102 is co-located with a camera 101 so that the camera can capture the "red-eye" effect of strobe illumination of the pupil. The detected pupil locations in the images are mapped to three-dimensional space, based upon the known positions and orientations of the cameras. Triangulation of the pupil data from the two cameras provides the spatial positions of the eyes. Next, image processing algorithms are performed on the captured images to identify ellipses that fit the edges of the iris. The ellipses provide the data needed for gaze direction determination.

In the example of FIG. 2, system 100 is used for gaze detection to a point on a computer screen. In this embodiment, system 100 achieves at least three objects: (1) locates the position on a display system where a person is looking; (2) provides inputs for adjusting the focal length of computer-generated graphics; and (3) provides computer pointer control as an alternative to a mouse or trackball.

In other applications, system 100 may be used for gaze detection to a distant point in space rather than to a display screen. That is, the gaze target need not be a predetermined distance from the eyes.

The two cameras simultaneously image the subject's face. An example of a suitable camera is a progressive scan video camera with a 60 Hz frame rate.

For computer control applications, cameras are mounted to the left and right of a computer monitor, nearly aligned with the monitor surface. In other applications, the cameras may be located in any convenient position in front of the viewer.

An example of a suitable image processing system is a computer with a 2.80 GHz Pentium 4 CPU with hyper-threading and an 800 MHz front-side bus. Configured with one GB RAM, a computer of this type had little difficulty processing 632×480 pixel image pairs at 30 Hz, often running at less than 10% CPU utilization during system operation. As explained below, accurate gaze detection may require higher resolution than 632×480, but image processing speeds are not believed to be problematic. The computer is programmed to perform the various processing algorithms described herein.

Image Acquisition

FIG. 3 illustrates one of the cameras 101 and its associated strobe light 102 in further detail. Strobe light 102 comprises a ring of LED lights, mounted around the camera lens. This configuration produces illumination that is close to coaxial with the camera's optical axis and effectively produces the red-eye effect. Near infra-red (NIR) illumination is invisible to the human eye, so the lighting system is not distracting to the subject. Each camera is fitted with an NIR filter that blocks visible light and transmits wavelengths produced by strobe light 102.

Referring to both FIGS. 2 and 3, the two strobe lights 102 are driven by a two-channel strobe controller 31. Greater illumination intensity is obtained by strobing the LEDs, and the short strobe period also helps freeze subject motion. The cameras ideally have a high NIR sensitivity, which allows smaller lens apertures to be used, increasing depth-of-field and image sharpness.

Lens focal length is selected to provide a field-of-view slightly wider than a subject's face. The selection of the size of the field of view may be a tradeoff between widening to accommodate the subject's motion versus achieving narrowing to achieve high spatial resolution for image analysis.

Image acquisition is achieved using a frame grabber 32, which simultaneously captures images from the two cameras 101. The frame grabber 32 also generates strobe trigger signals in synchronization with the camera timing.

Pupil Detection and Location in the Images

For pupil detection, an image with dark pupils (without red-eye) is subtracted from an image with bright pupils (with red-eye). The resulting image will have bright pupils, while regions illuminated similarly in the input images will be darker. Each bright-pupil image is obtained when the ring-light on the camera acquiring that image is strobed (fired). Each dark-pupil image is obtained when the ring-light on the camera not acquiring that image is fired. Thus, each strobe light 102 is fired on alternate frames so that a bright pupil image is acquired by one camera while the other camera simultaneously acquires a dark-pupil image.

The following table sets out the relationship of strobe operation to pupil image characteristic:

| Frame | Strobe Channel | Camera 1 | Camera 2 |
|---|---|---|---|
| 1 | Camera 1 | Bright Pupil | Dark Pupil |
| 2 | Camera 2 | Dark Pupil | Bright Pupil |
| 3 | Camera 1 | Bright Pupil | Dark Pupil |
| ... | ... | ... | ... |

Synchronization of the strobe channel with the acquired images is ensured by the image acquisition software so that the bright/dark pupil status of each image is known. Images are acquired into a circular buffer 34 so that both the most recent image and the previously acquired image can be used by the image processing system 35.

Figures 4A, 4B:
FIGS. 4A and 4B illustrate bright pupil and dark pupil images, respectively, acquired with the system of FIGS. 2 and 3.

FIGS. 4A and 4B illustrate bright pupil and dark pupil images, respectively. FIG. 4A was acquired with an on-camera strobe. FIG. 4B was acquired with an opposite-camera strobe. The images vary in their shadows and highlights. In particular, the pupils in FIG. 4A are bright whereas the pupils in FIG. 4B are dark.

Figure 5:
FIG. 5 illustrates the difference image obtained from FIGS. 4A and 4B.

FIG. 5 illustrates the difference image obtained by subtracting FIG. 4B from FIG. 4A. As explained above, in the configuration of FIG. 3, bright-pupil illumination is coaxial with the lens, while dark-pupil illumination is positioned to one side of the camera. This produces strong shadows in the dark-pupil image. In addition, highlight positions (from glossy and specular surfaces) varies between the two images due to the different locations of the illumination sources. The result is that the difference image (bright-pupil minus dark-pupil) contains significant bright regions in addition to the bright pupils.

In another embodiment, the illumination for each camera would be two concentric ring-lights, such that the small diameter ring produced bright pupils and the large diameter ring produced dark pupils. If the rings produced equal illumination intensity, the two images would be quite similar except for the red-eye effect, and as explained below, computing an image difference would yield a strong signal from the bright pupils.

Figure 6A:
FIGS. 6A and 6B illustrate the result of processing operations conducted on the difference image of FIG. 5, to identify the pupils and determine their location.
Figure 6B:

FIGS. 6A and 6B illustrate the result of processing operations conducted on the difference image of FIG. 5, to identify the pupils and determine their location. First, a threshold is applied to the difference image to create a binary image. Then morphological operations are used to fill holes and clean up edges. FIG. 6A illustrates the results of these operations.

Connectivity analysis is then conducted to group connected foreground pixels (white) into logical objects and measure their features. Measured features include area, aspect ratio, and position. Object features are then processed to identify the two objects corresponding to the pupils. Pupil size and shape is well constrained, so it is easy to eliminate large, small, and non-round objects from consideration. For the remaining objects, the expected distance between the pupils and their sizes were used to find the two pupils. FIG. 6B illustrates the results of these operations.

Figure 7:
FIG. 7 illustrates a subject's the two pupils located within one of the images.

FIG. 7 illustrates the two pupils located within one of the images.

Eye Position Triangulation

Figure 8:
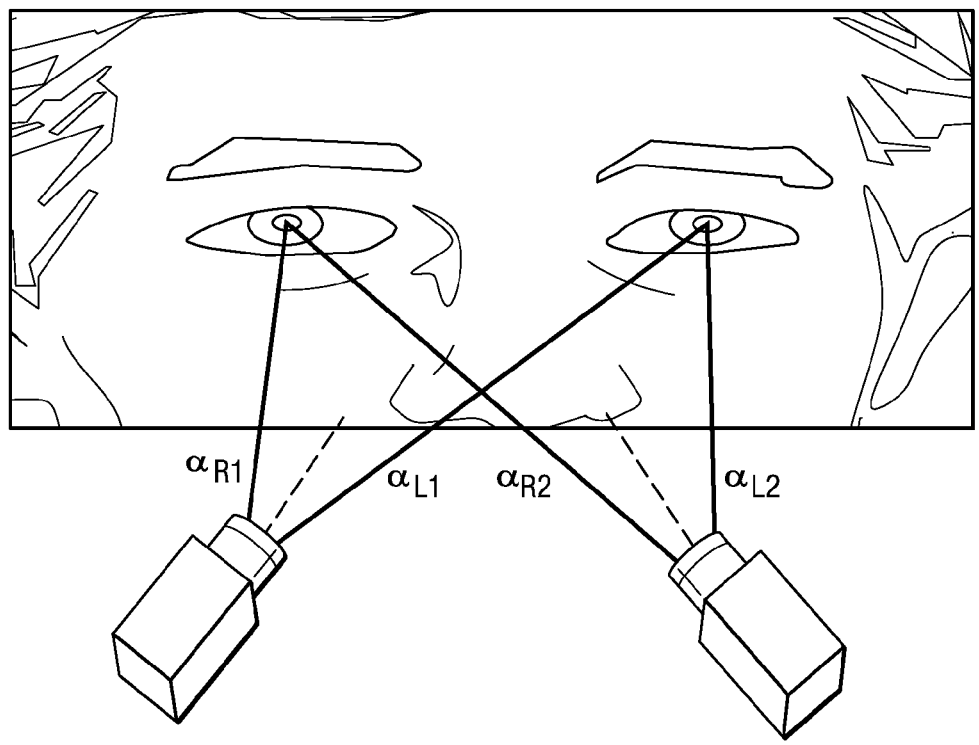
FIG. 8 illustrates how the eye positions are located in three-dimensional space, using triangulation.

As illustrated in FIG. 8, once the pupil locations in the two camera images are determined, the eye positions in three-dimensional (3D) space are computed using triangulation. Each pupil location in an image is measured as an azimuth and elevation angle offset from the camera centerline, based upon the camera lens field-of-view and pixel resolution. The angles are represented as unit direction vectors originating at the camera focal point. Lines along the left eye direction vectors are extended from each camera, and the three-dimensional point where the two lines come closest to intersecting is identified as the left eye position. The same process is followed to determine the right eye position.

Precise measurement of the camera positions and orientations is critical for the proper determination of the eye positions in 3D space. An automatic calibration process may be used to determine the positions, orientations, and fields-of-view of the cameras with minimal intervention. The calibration is performed by positioning a person at several different locations within the detection volume of the system. Then, pupil detection points are collected from the image pairs and saved as part of a calibration data set. Since a single individual is used to collect the calibration data set, then the inter-pupil distance is constant for all data points. A sweep through the set of possible camera positions and angles is performed to determine the triangulation errors for the data set. The camera calibration values are determined as the point where the least squares error for the calculated inter-pupil distance is minimized. Typically, the calibration values are read from a file upon system startup.

Calibration needs to occur only when a camera is moved. The calibration approach is automated and can be performed by any individual. Once calibrated, any number of different subjects can use the system without specific calibration for an individual.

Experimentation has indicated a high degree of accuracy in eye location according to the above-described technique. Due to the automated camera calibration approach, eye position triangulation errors are optimally minimized. One measurement of consistency, the standard deviation of the calculated inter-pupil distance, has been measured to be less than one one-hundredth of an inch on several occasions. No position bias or offset errors were observed.

Eye position measurement accuracy deteriorates when the cameras are placed closer together. This observation is logical when considering the triangulation approach.

Iris Edge Location; Gaze Detection

The next processing operation is finding the edges of the iris and fitting these edges to an ellipse. Pupil location is used to define a region-of-interest around the eye in which additional processing is performed to locate the edges of the iris.

Figure 9A:
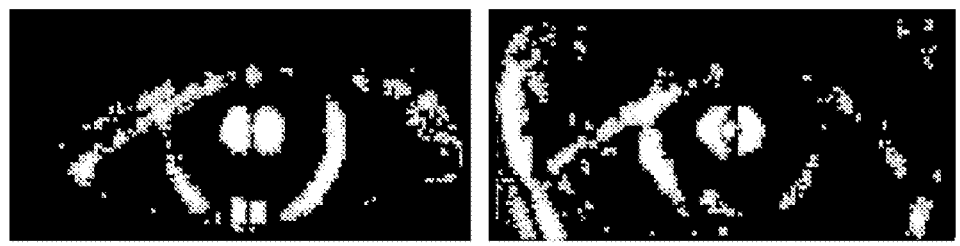
FIGS. 9A, 9B, and 9C illustrate processing operations for finding the edges of the subject's irises.
Figure 9B:

As illustrated in FIGS. 9A and 9B, first, horizontal and vertical image gradients are computed. These gradients are used as inputs to a Canny edge detector, which localizes edges to their maximum gradient and includes weaker edge points in the result if they are connected to a stronger edge.

Figure 9C:
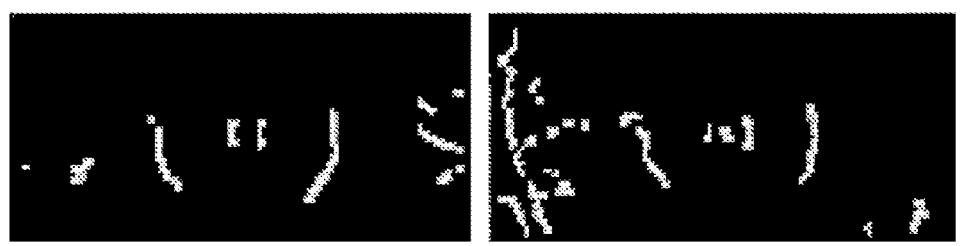

Results from the Canny detector are processed to select edges that were potential iris edges. It is expected that the eyelids will produce strong vertical gradients (horizontal edges) and these should be differentiated from the iris edges and not used for ellipse fitting. Also, the eyelids often cover the top and bottom of the iris, so only the side iris edges are attempted to be located. Edge orientation is computed from the horizontal and vertical gradients. Orientation is then used to filter the Canny edge results to keep only edges that are within 30° of a vertical orientation. FIG. 9C illustrates the results of this processing.

Connectivity analysis is then applied to the filtered edge results, which groups edge pixels in connected edge objects and measures several object features. The edges are then filtered by size, orientation, and position (expected distance from the pupil center) to identify the iris edges.

Figure 10:
FIG. 10 illustrates how the iris edges are fitted to ellipses.

As illustrated in FIG. 10, coordinates of points on the iris edges are then fit to an ellipse. Because ellipse fitting is sensitive to bad edge points that might be passed to the fitting algorithm, the result may be tested by comparing the ellipse center to the pupil location and comparing the ellipse major axis length to the expected iris diameter.

The task of ellipse fitting determines the two solutions of circles that produce the ellipse when projected onto the image plane. The normal to the plane of the circle (plane of the iris) is the gaze direction. The next task is to select the correct one of the two gaze direction vectors. There are two solutions from each of the two cameras. The gaze vectors can be converted to the system coordinate frame by factoring in the camera orientation. Only one gaze vector from each camera will be in agreement with a gaze vector from the other camera. Therefore the pair of gaze vectors that agree most closely are selected as the gaze solution.

Referring again to FIG. 1, the combination of eye locations and gaze angles define the gaze rays. The intersection of the gaze rays with the surface geometry of a known object can be computed. When the known object is a computer screen, the pixel at which the eyes are looking can be identified, described in terms of screen coordinates, and the location provided to an application program. As an enhancement, a subject's preference of one eye over another, if any, can be considered to properly select the point of visual attention.

Accuracy of gaze angle detection is expected to improve with image resolution. The number of image pixels available for the iris edge ellipse fit algorithm should be sufficient for consistent results. In one set of experiments, the diameter of the iris as it appears in the captured images was typically in the range of 40 to 50 pixels. As a result the chains of edge pixels identified by the Canny edge detector were too short for accurate ellipse fitting. An error of one pixel in measurement of the major or minor ellipse axis values can cause over a 15° gaze direction error. Also, situations when the subject's eyelids cover portions of the iris cause the edge pixel chains to be even shorter.

The frequency of ellipse fit solutions improves when the cameras are moved closer together, a direction opposite to increased eye position triangulation accuracy. An intermediate camera separation distance should be selected that adequately accommodates both accuracy requirements.

Potentially, the replacement of the cameras with higher resolution cameras would allow many more iris edge pixels to be detected and better ellipse fitting to be achieved. Evaluation of the performance improvement achieved from increased image resolution can be conducted by changing the system lenses and modifying software to image and process a single eye. Iris edge point locations are currently determined to one-pixel resolution. Additional image analysis could be conducted to locate iris edge points with sub-pixel resolution.

Applications

Gaze tracking could be used for numerous purposes in a desktop computing environment. Research into the human performance improvement with gaze tracking has been discussed. Also, the use of gaze tracking systems by handicapped users as an input control alternative should be explored.

It may be possible to use the positions of the eyes (without gaze direction) as an input to graphics and VR applications. For example, the eyes could be used to provide head position information in a constrained environment instead of magnetic head tracking devices that require users to wear head gear.

The eye positions could be used as an input to an autostereoscopic display system and an accurate gaze direction measurement could be used to accommodate adjustable focal length display systems.

In sum, the two-camera system design developed during this effort is unique compared to commercial products currently available. The strength of the system is that the position triangulation method provides a consistent starting point, rather than the rough estimate used in one-camera systems, for the eye gaze direction vector. Also, dual image processing leads to simplifications that allow higher frame rates.

What is claimed is:

1. A system for detecting eye location and gaze location of an animate subject, comprising:
   - a pair of cameras, one each for capturing images of one of the subject's eyes;
   - a pair of infrared illuminators, one each associated with a camera, operable to illuminate the subject's pupils;
   - an eye location image processing system operable to use the images from the cameras to locate the subject's pupils in two dimensional space, using a red-eye detection process, and to locate the subject's pupils in three dimensional space using a triangulation process based on the direction from the cameras to each pupil; and
   - a gaze direction processing system operable to use the same images to detect the gaze direction of the subject's eyes based on the shape of the subject's irises when projected onto the image plane.

2. The system of claim 1, wherein the gaze direction processing system uses an edge finding algorithm to find the edges of the eye's irises.

3. The system of claim 2, wherein the gaze direction processing system further uses a curve fitting algorithm to fit the iris edges to an ellipse.

4. The system of claim 1, wherein each illuminator comprises a ring of illumination sources around the lens of the camera.

5. The system of claim 1, wherein the triangulation process is further based on the distance between the subject's eyes.

6. The system of claim 1, wherein the illumination sources are LEDs.

7. A method for detecting eye location and gaze direction of an animate subject, comprising:
   - using a pair of cameras, one each for capturing images of one of the subject's eyes;
   - using a pair of infrared illuminators, one each associated with a camera, to illuminate the subject's pupils;
   - alternately illuminating the subject's eyes and synchronizing the cameras' image acquisition, such that a first camera acquires a bright image from its associated eye while a second camera acquires a dark image from its associated eye, then the first camera acquires a dark images of its associated eye while the second camera acquires a bright image of its associated eye;
   - using an eye location image processing system to locate the subject's pupils in two dimensional space by using a red-eye detection process, and to locate the subject's pupils in three dimensional space by using a triangulation process based on the direction from the cameras to each pupil; and
   - using a gaze direction processing system to use the same images to detect the gaze direction of the subject's eyes based on the shape of the subject's irises when projected onto the image plane.

8. The method of claim 7, wherein the gaze direction processing system uses an edge finding algorithm to find the edges of the eye's irises.

9. The method of claim 8, wherein the gaze direction processing system further uses a curve fitting algorithm to fit the iris edges to an ellipse.

* * * * *